US006875766B2

United States Patent
Turberg et al.

(10) Patent No.: US 6,875,766 B2
(45) Date of Patent: Apr. 5, 2005

(54) USE OF RIBOFLAVIN AND FLAVIN DERIVATIVES AS CHITINASE INHIBITORS

(75) Inventors: Andreas Turberg, Haan (DE); Volker Gutsmann, Leichlingen (DE); Satosho Omura, Tokyo (JP); Kazuro Shiomi, Tokyo (JP)

(73) Assignee: Bayer AG, Leverkusan (DE)

( * ) Notice: Subject to any disclaimer, the term of this patent is extended or adjusted under 35 U.S.C. 154(b) by 0 days.

(21) Appl. No.: 10/380,651

(22) PCT Filed: Sep. 10, 2001

(86) PCT No.: PCT/EP01/10425

§ 371 (c)(1),
(2), (4) Date: Mar. 14, 2003

(87) PCT Pub. No.: WO02/23991

PCT Pub. Date: Mar. 28, 2002

(65) Prior Publication Data

US 2003/0191091 A1 Oct. 9, 2003

(30) Foreign Application Priority Data

Sep. 19, 2000 (DE) .......................... 100 46 267

(51) Int. Cl.$^7$ ..................... A01N 43/60; A61K 31/495

(52) U.S. Cl. ..................................................... 514/250
(58) Field of Search .......................................... 514/250

(56) References Cited

U.S. PATENT DOCUMENTS 4,602,931 A * 7/1986 Pfister et al. ................. 71/86

FOREIGN PATENT DOCUMENTS

| CN | 1205167 | * | 1/1999 |
| DE | 4139752 | | 10/1992 |
| FR | 2760941 | | 9/1998 |
| HU | 45187 | * | 6/1988 |
| WO | 9933812 | * | 7/1999 |
| WO | 0004930 | | 2/2000 |
| WO | WO-00/04930 | * | 2/2000 |

OTHER PUBLICATIONS

Aver'yanov et al, Active oxygen–associated control of rice blast disease by riboflavin and roseoflavin, 2000, Biochemistry (Moscow), 65(11), 1292–8.*

* cited by examiner

Primary Examiner—Alton Pryor

(57) ABSTRACT

The invention relates to the use of riboflavin and of flavin derivatives with chitinase-inhibitory action for controlling arthropods, nematodes and chitin-containing fungi.

4 Claims, No Drawings

USE OF RIBOFLAVIN AND FLAVIN DERIVATIVES AS CHITINASE INHIBITORS

The invention relates to the use of riboflavin and of flavin derivatives with chitinase-inhibitory action for controlling arthropods, nematodes and chitin-containing fungi.

In the field of agriculture, arthropods constitute a worldwide problem for food production and the health of humans and animals since they are plant pests, parasites and hygiene pests.

Besides traditional nature-based approaches, synthetic chemicals have been used intensively for approximately 60 years only. However, virtually all pests develop resistances or tolerances to the active compounds, in particular when the latter are employed continuously. The mechanisms by which the active compounds are neutralized are varied, ranging from simple behavioral changes via uptake barriers and the metabolism to the insensitivity of the actual target protein of the substances.

To support existing treatment schemes, it is therefore extremely important to find new mechanisms of action with new classes of active compounds and to optimize the useful life of these new substances by combination or rotation with known structures.

It is generally known that arthropods have an exoskeleton, which distinguishes them from most other life forms. An important constituent of this arthropod cuticula is chitin. It is likewise known that arthropods must change this rigid cuticle repeatedly during their development from the larva to the adult in order to be able to grow. This process, termed ecdysis, is subject to complex hormonal regulation, during which a variety of proteins are formed or repressed. Some of these proteins are responsible for the degradation of old cuticula and cuticular resynthesis [K-D. Spindler, In: K. Scheller (ed.) The larval serum proteins of insects. Thieme, Stuttgart: 135–150 (1983)].

Thus, the cuticular component chitin, a β-1-4-N-acetylglucosamine homopolymer, supplies the N-acetylglucosamine units required for chitin resynthesis in the endocuticular layer. To this end, the epidermis underneath the cuticula excretes chitin-digesting enzymes at the time of ecdysis. These chitinases cleave the chitin polymer at random sites down to dimers of N-acetylglucosamine=chitobiose (endochitinases 3.2.1.14) and N-acetylglucosamine. The cleavage of the dimers to N-acetylglucosamine monomers, and the elimination of N-acetylglucosamine from the non-reducing end of the chitin chain (exochitinase reaction) is also catalyzed by N-acetylglucosaminidases=hexasaminidases (3.2.1.50).

However, chitin is not only found in arthropods. It is also an important component of the fungal cell walls. Chitin and chitinolytic activity were also found in nematodes. Thus, substances which engage in the chitin metabolism are not suitable for controlling arthropods, but also for use as fungicides or nematicides.

It has already been suggested repeatedly in the literature to employ the chitin metabolism as starting point for the development of new and fresh pesticides [Spindler, K-D., Spindler-Barth, M. & M. Londershausen, Parasitol. Res. 76:283–288 (1990); E. Cohen, Arch. Insect Biochem. Physiol. 22: 245–261 (1993)]. A commercially exploitable class of substances which has an effect on chitin biosynthesis was found for the first time in the benzoylphenylureas. However, no commercially suitable substances which directly inhibit chitin synthase (EC 3.2.1.16) have been available to date. While inhibitors of chitinase (EC 3.2.1.14) have been described, their commercial use has not been possible to date owing to insufficient in vivo activity [Sakuda, S., A. Isogai, S. Matsumoto, A. Suzuki & K. Koseki, Tetra-hedron Lett. 27, 2475–2478 (1986); Koga, D., A. Isogai, S. Sakuda, S. Matsumoto, A. Suzuki, S. Kimura & A. Ide, Agric. Biol. Chem. 51, 471–476 (1987)].

A sensitive measurement principle for the specific determination of endochitinase activities in small volumes is already known in principle [McCreath, K. J. & G. W. Gooday, J. Microbiol. Meth. 14, 229–237 (1992)].

The search for new chitinase inhibitors which are suitable for controlling pests is therefore of great interest.

The invention therefore relates to the use of flavin derivatives of the formula (I)

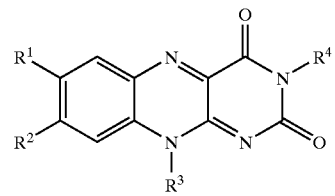

in which

R$^1$ is hydrogen, trifluoromethyl, alkyl or alkoxy,

R$^2$ is hydrogen, halogen, preferably chlorine, nitro, alkyl, alkoxy, dialkylamino, preferably dimethylamino, —CH$_2$COOH or the radical NHCH$_2$CH(OH)CH(OH)CH(OH)CH$_2$OH, R$^3$ is hydrogen, CH$_2$CH$_2$CH(OH)CH(OH)CH$_2$OH, CH$_2$CH(OH)CH(OH)CH(OH)CH$_2$OH, phenyl, —CH$_2$CHO, —CH$_2$CH$_2$OH, CH$_2$CH(OH)CH(OH)CH(OH)CH(OH)CH$_3$ or CH$_2$CH(OH)CH(OH)CH(OH)CH$_2$OPO$_3$, R$^4$ is hydrogen or alkyl and of their stereoisomers and salts for controlling pests.

Compounds of the formula (I) which are preferably employed in accordance with the invention are those in which R$^1$ is methyl R$^2$ is methyl, dimethylamino or NHCH$_2$CH(OH)CH(OH)CH(OH)CH$_2$OH R$^3$ is CH$_2$CH$_2$CH(OH)CH(OH)CH$_2$OH or CH$_2$CH(OH)CH(OH)CH(OH)CH$_2$OH R$^4$ is hydrogen and their stereoisomers and salts.

The compounds of the formula (I) according to the invention can exist in various stereoisomeric forms which behave either like image and mirror image (enantiomers) or which do not behave like image and mirror image (diastereomers). The invention relates both to the enantiomers and to the diastereomers and their respective mixtures. The racemic forms, like the diastereomers, can be resolved in the known manner to give the stereoisomerically uniform components.

Moreover, certain compounds can exist in tautomeric forms. The skilled worker is familiar herewith, and such compounds likewise fall within the scope of the invention.

The compounds according to the invention can also exist in the form of salts. Physiologically acceptable salts are preferred for the purposes of the invention.

Physiologically acceptable salts can be salts of the compounds according to the invention with inorganic or organic acids. Salts with inorganic acids such as, for example, hydrochloric acid, hydrobromic acid, phosphoric acid or sulfuric acid, or salts with organic carboxylic acids or sulfonic acids such as, for example, acetic acid, propionic acid, maleic acid, fumaric acid, malic acid, citric acid, tartaric acid, lactic acid, benzoic acid or methanesulfonic acid, ethanesulfonic acid, benzenesulfonic acid, toluenesulfonic acid or naphthalenedisulfonic acid are preferred.

Likewise, physiologically acceptable salts can be salts of the compounds according to the invention with bases, such as, for example, metal salts or ammonium salts. Preferred examples are alkali metal salts (for example sodium or potassium salts), alkaline earth metal salts (for example magnesium or calcium salts) and ammonium salts which are derived from ammonia or organic amines such as, for example, ethylamine, di- or triethylamine, ethyldiisopropylamine, ethanolamine, di- or triethanolamine, dicyclohexylamine, dimethylaminoethanol, dibenzylamine, N-methylmorpholine, dihydroabietylamine, 1-ephenamine, methylpiperidine, arginine, lysine, ethylenediamine or 2-phenylethylamine.

For the purposes of the invention, alkyl is a straight-chain or branched alkyl radical, preferably having up to 6, especially preferably up to 4, very especially preferably up to 3, carbon atoms. Examples which may be mentioned are: methyl, ethyl, n-propyl, isopropyl, t-butyl, n-pentyl and n-hexyl.

Alkoxy is a straight-chain or branched alkoxy radical, preferably having up to 6, especially preferably up to 4, very especially preferably up to 3, carbon atoms. Examples which may be mentioned are: methoxy, ethoxy, n-propoxy, isopropoxy, tert-butoxy, n-pentoxy and n-hexoxy.

For the purposes of the invention, dialkylamino is an amino group having two identical or different straight-chain or branched alkyl substituents, each of which has preferably up to 6, especially preferably up to 4, very especially preferably up to 3, carbon atoms. Examples which may be mentioned are: N,N-dimethylamino, N,N-diethylamino, N-ethyl-N-methylamino, N-methyl-N-n-propylamino, N-isopropyl-N-n-propylamino, N-t-butyl-N-methyl amino, N-ethyl-N-n-pentylamino and N-n-hexyl-N-methylamino.

The compound riboflavin has been known for a long time (see, for example, Merck Index, 12$^{th}$ edition 1996, Entry No. 8367, p. 1410). It is the compound of the formula (I) in which $R^1$ and $R^2$ are in each case methyl $R^3$ is the radical of the formula

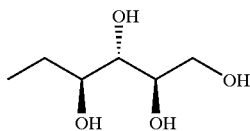

and $R^4$ is hydrogen.

The chitinase inhibitory activity was determined as already described [Omura, S., Arai, N., Yamaguchi, Y., Masuma, R., Iwai, Y., Namikoshi, M., Turberg, A., Kölbl, H., Shiomi, K., J. Antibiot., 53, 603–608 (2000)]. The IC$_{50}$ values of riboflavin against *Lucilia cuprina* chitinase were determined at 37° C. as 2.1 µM and at 20° C. as 0.38 µM, but no inhibition of the *Streptomyces griseus* chitinase (Sigma) or the *Vibrio alginolyticus* chitinase (Kyowa Medex) was measured at 100 µM (37° C.).

It is known from the literature that riboflavin must have essential tasks in the insect. Several studies have revealed that the addition of riboflavin to feed (natural or artificial rations) have a positive effect on larval development and on the fertility of adult insects of various species. It is thus surprising, even for the skilled worker, that riboflavin and riboflavin derivatives inhibit an essential enzyme in the developmental pattern of arthropods in the µM range and in some cases bring about an inhibition of the ecdysis process when insect larvae are treated [Saksena, C. & S. L. Perti., Labdev J. Sci. Tech. 9-B, 126–131 (1971)].

Several authors found that, while riboflavin is present in the hemolymphs at relatively high concentrations, 100% of it is bound to proteins [Miller, S. G. & D. L. Silhacek, Insect Biochem. Molec. Biol. 22, 571–583 (1992)]. The binding of riboflavin is generally assumed to have a storage function; in this way, vitamin B2, which is essential, is also to be available in sufficient quantity during those developmental phases in which no food can be taken up.

If riboflavin, or flavin derivatives, which are capable of crossing the cuticula and reaching the epidermis or which penetrate the gut in sufficiently high concentration are found, these derivatives can inhibit the degradation of the endocuticular layer, owing to inhibition of the chitinases, and thus interfere with ecdysis. As a consequence, the arthropod will eventually synthesize a new cuticula, but will not be able to leave the old cuticula, or all of the old cuticula, behind. Growth and the uptake of food are prevented and, eventually, the arthropod dies.

In principle, representatives of the type of the compounds of the formula (I) are capable of inhibiting chitinases from arthropods, nematodes and fungi. They are thus suitable for use as arthropodicides, nematicides and fungicides.

The active compounds are suitable for controlling animal pests, in particular insects, arachnids and nematodes, which are found in agriculture, in forests, in the protection of stored products and of materials, and in the hygiene sector, while being well tolerated by plants and having favorable toxicity to warm-blooded species. They can preferably be employed as crop protection agents or veterinary medicines for livestock and pets and in animal-house and domestic hygiene. They are effective against normally sensitive and resistant species, and against all or individual developmental stages. The abovementioned pests include:

From the order of the *Isopoda*, for example *Oniscus asellus, Armadillidium vulgare, Porcellio scaber.*

From the order of the *Diplopoda*, for example *Blaniulus guttulatus.*

From the order of the *Chilopoda*, for example *Geophilus carpophagus, Scutigera*spp.

From the order of the *Symphyla*, for example *Scutigerella immaculata.*

From the order of the *Thysanura*, for example *Lepisma saccharina.*

From the order of the *Collembola*, for example *Onychiurus armatus.*

From the order of the *Orthoptera*, for example *Acheta domesticus, Gryllotalpa* spp., *Locusta migratoria migratorioides, Melanoplus* spp., *Schistocerca gregaria.*

From the order of the *Blattaria*, for example *Blatta orientalis, Periplaneta americana, Leucophaea maderae, Blattella germanica.*

From the order of the *Dermaptera*, for example *Forficula auricularia.*

From the order of the *Isoptera*, for example *Reticulitermes* spp.

From the order of the *Phthiraptera*, for example *Pediculus humanus corporis, Haematopinus* spp., *Linognathus* spp., *Trichodectes* spp., *Damalinia* spp.

From the order of the *Thysanoptera*, for example *Hercinothrips femoralis, Thrips tabaci, Thrips palmi, Frankliniella accidentalis.*

From the order of the *Heteroptera,* for example *Eurygaster* spp., *Dysdercus intermedius, Piesma quadrata, Cimex lectularius, Rhodnius prolixus, Triatoma* spp.

From the order of the *Homoptera,* for example *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.

From the order of the *Lepidoptera,* for example *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera*spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of the *Coleoptera,* for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptrus oryzophilus.*

From the order of the *Hymenoptera,* for example *Diprion* spp., *Hoplocampa* spp., *Lasius* spp., *Monomorium pharaonis, Vespa* spp.

From the order of the *Diptera,* for example *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hypobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp.

From the order of the *Siphonaptera,* for example *Xenopsylla cheopis,* Ceratophyllus spp.

From the class of the *Arachnida,* for example *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera*spp., *Meloidogyne* spp., *Aphelenchoides* spp., *Longidorus* spp., *Xiphinema* spp., *Trichodorus* spp., *Bursaphelenchus* spp.

The compounds of the formula (I) of the invention are distinguished in particular by their inhibitory effect on dipteran endochitinases and by their effect on larval developmental stages of representatives of the order Blattaria.

If appropriate, the compounds according to the invention, when applied in specific concentrations and at specific rates, can also be used as herbicides and as microbicides, for example as fungicides, antimycotics and bactericides. If appropriate, they can also be employed as intermediates and precursors for the synthesis of active compounds.

All plants and plant parts can be treated in accordance with the invention. Plants in this context are taken to mean all plants and plant populations, such as desired and undesired wild plants or crop plants (including naturally occurring crop plants). Crop plants can be plants which can be obtained by conventional breeding and optimization methods, or by biotechnological and recombinant methods, or by combinations of these methods, including the transgenic plants and including the plant varieties which are capable, or incapable, of being protected by Plant Breeders' Rights. Plant parts are taken to mean all aerial and subterranean parts and organs of the plants, such as shoot, leaf, flower and root, examples mentioned being leaves, needles, stalks, stems, flowers, fruiting bodies, fruits and seeds, and also roots, tubers and rhizomes. The plant parts also include harvested material and vegetative and generative propagation material, for example cuttings, tubers, rhizomes, offshoots and seeds.

Treatment according to the invention of the plants or plant parts with the active compounds is performed either directly or by exposure of their environment, habitat or store by the customary treatment methods, for example by dipping, spraying, releasing vapor, fogging, spreading, brushing on and, in the case of propagation material, in particular of seeds, furthermore by applying one or more coats.

The active compounds can be converted into the customary formulations, such as solutions, emulsions, wettable powders, suspensions, powders, dusts, pastes, soluble powders, granules, suspoemulsion concentrates, natural and synthetic material impregnated with active compounds and microencapsulations in polymeric substances.

These formulations are produced in a known manner, for example by mixing the active compounds with extenders, that is liquid solvents and/or solid carriers, optionally with the use of surfactants, that is, emulsifiers and/or dispersants and/or foam formers.

In the case of the use of water as extender, organic solvents can, for example, also be used as cosolvents. The following are mainly suitable as liquid solvents: aromatics such as xylene, toluene or alkylnaphthalenes, chlorinated aromatic or chlorinated aliphatic hydrocarbons, such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are:
for example ammonium salts and ground natural minerals such as kaolins, clays, talc, chalk, quartz, attapulgite, montmorillonite or diatomaceous earth, and ground synthetic minerals such as highly disperse silica, alumina and silicates, suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulfonates, alkylsulfates, arylsulfonates, or else protein hydrolyzates; suitable dispersants are: for example lignin-sulfite waste liquors and methylcellulose.

Adhesives such as carboxymethylcellulose, and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compound according to the invention, in its commercially available formulations and in the use forms prepared from these formulations, can be used in a mixture with other active compounds, such as insecticides, attractants, sterilants, bactericides, acaricides, nematicides, fungicides, growth regulators or herbicides. The insecticides include, for example, phosphoric esters, carbamates, carboxylic esters, chlorinated hydrocarbons, phenylureas, substances produced by microorganisms and the like.

Examples of suitable components in mixtures are the following:

Fungicides:
- aldimorph, ampropylfos, ampropylfos-potassium, andoprim, anilazin, azaconazole, azoxystrobin,
- benalaxyl, benodanil, benomyl, benzamacril, benzamacryl-isobutyl, bialaphos, binapacryl, biphenyl, bitertanol, blasticidin-S, bromuconazole, bupirimate, buthiobate,
- calcium polysulfide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
- debacarb, dichlorophen, diclobutrazole, diclofluanid, diclomezin, dicloran, diethofencarb, difenoconazole, dimethirimol, dimethomorph, diniconazole-M
- dinocap, diphenylamine, dipyrithione, ditalimfos, dithianon, dodemorph, dodine, drazoxolon,
- ediphenphos, epoxiconazole, etaconazole, ethirimol, etridiazole,
- famoxadon, fenapanil, fenarimol, fenbuconazole, fenfuram, fenitropan, fenpiclonil, fenpropidin, fenpropimorph, fentin acetate, fentin hydroxide, ferbam, ferinmzone, fluazinam, flumetover, fluoromid, fluquinconazole, flurprimidol, flusilazole, flusulfamide, flutolanil, flutriafol, folpet, fosetyl-alminium, fosetyl-sodium, fthalide, fuberidazole, furalaxyl, furametpyr, furcarbonil, furconazole, furconazolecis, furmecyclox,
- guazatine,
- hexachlorobenzene, hexaconazole, hymexazole,
- imazalil, imibenconazole, iminoctadin, iminoctadin albesilate, iminoctadin triacetate, iodocarb, ipconazole, iprobenfos (IBP), iprodione, irumamycin, isoprothiolan, isovaledione,
- kasugamycin, kresoxim-methyl, copper preparations such as: copper hydroxide, copper naphthenate, copper oxychloride, copper sulfate, copper oxide, oxine-copper and Bordeaux mixture,
- mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
- nickel dimethyldithiocarbamate, nitrothal-isopropyl, nuarimol,
- ofurace, oxadixyl, oxamocarb, oxolinic acid, oxycarboxim, oxyfenthiin,
- paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
- quinconazole, quintozene (PCNB),
- sulfur and sulfur preparations,
- tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole,
- uniconazole,
- validamycin A, vinclozolin, viniconazole,
- zarilamid, zineb, ziram and
- Dagger G,
- OK-8705,
- OK-8801,
- α-(1,1-dimethylethyl)-β-(2-phenoxyethyl)-1H-1,2,4-triazole-1-ethanol,
- α-(2,4-dichlorophenyl)-β-fluoro-b-propyl-1H-1,2,4-triazole-1-ethanol,
- α-(2,4-dichlorophenyl)-β-methoxy-a-methyl-1H-1,2,4-triazole-1-ethanol,
- α-(5-methyl-1,3-dioxan-5-yl)-β-[[4-(trifluoromethyl)-phenyl]-methylene]-1H-1,2,4-triazole-1-ethanol,
- (5RS,6RS)-6-hydroxy-2,2,7,7-tetramethyl-5-(1H-1,2,4-triazol-1-yl)-3-octanone,
- (E)-a-(methoxyimino)-N-methyl-2-phenoxy-phenylacetamide,
- 1-isopropyl {2-methyl-1-[[[1-(4-methylphenyl)-ethyl] amino]-carbonyl]-propyl}-carbamate,
- 1-(2,4-dichlorophenyl)-2-(1H-1,2,4-triazol-1-yl)-ethanone O-(phenylmethyl)-oxime,
- 1-(2-methyl-1-naphthalenyl)-1H-pyrrole-2,5-dione,
- 1-(3,5-dichlorophenyl)-3-(2-propenyl)-2,5-pyrrolidinedione,
- 1-[(diiodomethyl)-sulfonyl]4-methyl-benzene,
- 1-[[2-(2,4-dichlorophenyl)-1,3-dioxolan-2-yl]-methyl]-1H-imidazole, 1-[[2-(4-chlorophenyl)-3-phenyloxiranyl]-methyl]1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinol,
2',6'-dibromo-2-methyl-4'-trifluoromethoxy-4'-trifluoromethyl-1,3-thiazole-5-carboxanilide,
2,2-dichloro-N-[1-(4-chlorophenyl)-ethyl]1-ethyl-3-methylcyclopropanecarboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulfonyl]-5-(trichloromethyl)-1,3,4-thiadiazole,
2-[[6-deoxy-4-O-(4-O-methyl-β-D-glycopyranosyl)-a-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol(OPP),
3,4-dichloro-1-[4-(difluoromethoxy)-phenyl]-1H-pyrrole-2,5-dione,
3,5-dichloro-N-[cyano[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulfonamide,
4-methyl-tetrazolo[1,5-a]quinazolin-5(4H)-one,
8-(1,1-dimethylethyl)-N-ethyl-N-propyl-1,4-dioxaspiro[4,5]decane-2-methanamine,
8-hydroxyquinoline sulfate,
N-2-[(phenylamino)-carbonyl]-9H-xanthene-9-carbohydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine hydrochloride,
ethyl[(4-chlorophenyl)-azo]-cyanoacetate,
potassium hydrogen carbonate,
sodium methanetetrathiolate,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide.
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)4-methyl-3-nitro-benzenesulfonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro4,5-bis-(2-propinyloxy)-phenyl]-N'-methoxy-methanimideamide,
sodium N-formyl-N-hydroxy-DL-alaninate,
O,O-diethyl[2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran]-3'-one,
Bactericides:
  bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulfate and other copper preparations.
Insecticides/acaricides/nematicides:
  abamectin, acephate, acetamiprid, acrinathrin, alanycarb, aldicarb, aldoxycarb, alphacypermethrin, alphamethrin, amitraz, avermectin, AZ 60541, azadirachtin, azamethiphos, azinphos A, azinphos M, azocyclotin,
  *Bacillus popilliae, Bacillus sphaericus, Bacillus subtilis, Bacillus thuringiensis, baculoviruses, Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben,
  cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine,
  deltamethrin, demeton M, demeton S, demeton-S-methyl, diafenthiuron, diazinon, dichlorvos, diflubenzuron, dimethoate, dimethylvinphos, diofenolan, disulfoton, docusate sodium, dofenapyn,
  eflusilanate, emamectin, empenthrin, endosulfan, *Entomopfthora* spp., eprinomectin, esfenvalerate, ethiofencarb, ethion, ethoprophos, etofenprox, etoxazole, etrimfos,
  fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses halofenozide, HCH, heptenophos, hexaflumuron, hexythiazox, hydroprene, imidacloprid, isazofos, isofenphos, isoxathion, ivermectin, nuclear polyhedrosis viruses lambda-cyhalothrin, lufenuron malathion, mecarbam, metaldehyde, methamidophos, *Metharhizium anisopliae, Metharhizium flavoviride*, methidathion, methiocarb, methomyl, methoxyfenozide, metolcarb, metoxadiazone, mevinphos, milbemectin, monocrotophos, naled, nitenpyram, nithiazine, novaluron omethoate, oxamyl, oxydemethon M

*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen, quinalphos, ribavirin salithion, sebufos, selamectin, silafluofen, spinosad, sulfotep, sulprofos, tau-fluvalinate, tebufenozide, tebufenpyrad, tebupirimiphos, teflubenzuron, tefluthrin, temephos, temivinphos, terbufos, tetrachlorvinphos, thetacypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii* zeta-cypermethrin, zolaprofos (1R-cis)-[5-(phenylmethyl)-3-furanyl]-methyl 3-[(dihydro-2-oxo-3(2H)-furanylidene)-methyl]-2,2-dimethylcyclopropanecarboxylate (3-phenoxyphenyl)-methyl 2,2,3,3-tetramethylcyclopropanecarboxylate 1-[(2-chloro-5-thiazolyl)methyl]tetrahydro-3,5-dimethyl-N-nitro-1,3,5-triazine-2(1H)-imine 2-(2-chloro-6-fluorophenyl)-4-[4-(1,1-dimethylethyl)phenyl]-4,5-dihydro-oxazole 2-(acetyloxy)-3-dodecyl-1,4-naphthalenedione 2-chloro-N-[[[4-(1-phenylethoxy)-phenyl]-amino]-carbonyl]-benzamide 2-chloro-N-[[[4-(2,2-dichloro-1,1-difluoroethoxy)-phenyl]-amino]-carbonyl]-benzamide 3-methylphenyl propylcarbamate 4-[4-(4-ethoxyphenyl)-4-methylpentyl]-1-fluoro-2-phenoxy-benzene 4-chloro-2-(1,1-dimethylethyl)-5-[[2-(2,6-dimethyl-4-phenoxyphenoxy)ethyl]thio]-3(2H)-pyridazinone 4-chloro-2-(2-chloro-2-methylpropyl)-5-[(6-iodo-3-pyridinyl)methoxy]-3(2H)-pyridazinone 4-chloro-5-[(6-chlor-3-pyridinyl)methoxy]-2-(3,4-dichlorophenyl)-3(2H)-pyridazinone

*Bacillus thuringiensis* strain EG-2348

N-[2-benzoyl-1-(1,1-dimethylethyl)-benzohydrazide 2,2-dimethyl-3-(2,4-dichlorophenyl)-2-oxo-1-oxaspiro[4,5]dec-3-en-4-yl butanoate

[3-[(6-chloro-3-pyridinyl)methyl]-2-thiazolidinylidene]-cyanamide dihydro-2-(nitromethylene)-2H-1,3-thiazine-3(4H)-carboxaldehyde ethyl[2-[[1,6-dihydro-6-oxo-1-(phenylmethyl)-4-pyridazinyl]oxy]ethyl]-carbamate N-(3,4,4-trifluoro-1-oxo-3-butenyl)-glycine N-(4-chlorophenyl)-3-[4-(difluoromethoxy)phenyl]-4,5-dihydro-4-phenyl-1H-pyrazole-1-carboxamide N-[(2-chloro-5-thiazolyl)methyl]-N'-methyl-N"-nitroguanidine N-methyl-N'-(1-methyl-2-propenyl)-1,2-hydrazinedicarbothioamide N-methyl-N'-2-propenyl-1,2-hydrazinedicarbothioamide O,O-diethyl[2-(dipropylamino)-2-oxoethyl]-ethylphosphoramidothioate A mixture with other known active compounds such as herbicides, or with fertilizers and growth regulators, is also possible.

When used as insecticides, the active compounds according to the invention in their commercially available formulations and in the use forms which are prepared from these formulations may furthermore be present as a mixture with synergists. Synergists are compounds by which the action of the active compounds is increased without it being necessary for the synergist added to be active itself.

The active compound content of the use forms prepared from the commercially available formulations can vary within wide ranges. The active compound concentration of the use forms can amount to from 0.0000001 to 95% by weight of active compound, preferably between 0.0001 and 1% by weight.

They are applied in a customary manner adapted to suit the use forms.

When applied against hygiene and stored-product pests, the active compound is distinguished by outstanding residual action on wood and clay and by good stability to alkali on limed substrates.

The active compounds according to the invention are not only active against plant, hygiene and stored-product pests, but also, in the veterinary medicine sector, against animal parasites (ectoparasites) such as hard ticks, soft ticks, scab mites, harvest mites, flies (stinging and licking), parasitic fly larvae, lice, hair lice, feather lice and fleas. These parasites include:

From the order of the *Anoplurida*, for example *Haematopinus* spp., *Linognathus* spp., *Pediculus* spp., *Phtirus* spp., *Solenopotes* spp.

From the order of the *Mallophagida* and the suborders *Amblycerina* and *Ischnocerina*, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order *Diptera* and the suborders *Nematocerina* and *Brachycerina*, for example *Aedes* pp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the *Siphonapterida*, for example *Pulex* spp., *Ctenocephalides* spp., *Xenopsylla* spp., *Ceratophyllus* spp.

From the order of the *Heteropterida*, for example *Cimex* spp., *Triatoma* spp., *Rhodnius* spp., *Panstrongylus* spp.

From the order of the *Blattarida*, for example *Blatta orientalis, Periplaneta americana, Blattela germanica, Supella* spp.

From the subclass of the *Acaria (Acarida)* and the orders of the *Meta* and *Mesostigmata*, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the *Actinedida (Prostigmata)* and *Acaridida (Astigmata)*, for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula (I) according to the invention are also suitable for controlling arthropods which infest agricultural livestock such as, for example, cattle, sheep, goats, horses, pigs, donkeys, camels, buffaloes, rabbits, chickens, turkeys, ducks, geese, honeybees, other domestic animals such as, for example, dogs, cats, cage birds, aquarium fish, and also what are known as experimental animals such as, for example, hamsters, guinea pigs, rats and mice. By controlling these arthropods, cases of death and reduction in productivity (for meat, milk, wool, hives, eggs, honey and the like), should be diminished so that more economical and simpler animal husbandry is possible by the use of the active compounds according to the invention.

The active compounds according to the invention are used in the veterinary sector in a known manner by enteral administration in the form of, for example, tablets, capsules, potions, drenches, granules, pastes, boluses, the feed-through method, and suppositories, by parenteral administration such as, for example, by injections (intramuscular, subcutaneous, intravenous, intraperitoneal and the like), implants, by nasal administration, by dermal use in the form, for example, of dipping or bathing, spraying, pouring on and spotting on, washing and powdering, and also with the aid of molded articles comprising active compound, such as collars, ear marks, tail marks, limb bands, halters, marking devices and the like.

When used for livestock, poultry, domestic animals and the like, the active compounds of the formula (I) can be used as formulations (for example powders, emulsions, flowables) comprising the active compounds in an amount of from 1 to 80% by weight, directly or after 100- to 10 000-fold dilution, or else they may be used as a chemical bath.

Moreover, it has been found that the compounds according to the invention have a potent insecticidal action against insects which destroy industrial materials.

The following insects may be mentioned by way of example and by preference, but without limitation:

Beetles such as *Hylotrupes bajulus, Chlorophorus pilosis, Anobium punctatum, Xestobium rufovillosum, Ptilinus pecticomis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus.*

Hymenopterans such as *Sirex juvencus, Urocerus gigas, Urocerus gigas taignus, Urocerus augur.*

Termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.* Bristletails such as *Lepisma saccharina.*

Industrial materials are to be understood as meaning, in the present context, non-live materials such as, preferably, plastics, adhesives, sizes, paper and board, leather, wood, timber products and paints.

The material to be protected from attack by insects is very particularly preferably wood and timber products.

Wood and timber products which can be protected by the agent according to the invention or by mixtures comprising this agent are to be understood as meaning, for example:

construction timber, wooden beams, railway sleepers, bridge components, jetties, wooden vehicles, boxes, pallets, containers, telephone poles, wooden claddings, windows and doors made from wood, or plywood, chipboard, joiners' work or timber materials which, quite generally, are used in domestic construction or in joinery.

The active compounds can be used as such, in the form of concentrates or generally customary formulations such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellant, if appropriate desiccants and UV stabilizers, and, if appropriate, dyes and pigments and other processing auxiliaries.

The insecticides or concentrates used for the protection of wood and timber products comprise the active compound according to the invention in a concentration of from 0.0001 to 95% by weight, in particular 0.001 to 60% by weight.

The amount of agents or concentrates employed depends on the species and the abundance of the insects and on the medium. The optimal amount used can be determined by test series upon application. However, in general it will suffice to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier or wetter.

Organochemical solvents which are preferably employed are oily or oil-type solvents with an evaporation number of above 35 and a flash point of above 30° C., preferably above 45° C. Such water-insoluble, oily and oil-type solvents of low volatility which are used are suitable mineral oils or their aromatic fractions and mineral-oil-containing solvent mixtures, preferably white spirit, petroleum and/or alkylbenzene.

Mineral oils which are preferably used are those with a boiling range of from 170 to 220° C., white spirit with a boiling range of from 170 to 220° C., spindle oil with a boiling range of from 250 to 350° C., petroleum and aromatics with a boiling range of from 160 to 280° C., oil of turpentine and the like.

In a preferred embodiment, liquid aliphatic hydrocarbons with a boiling range of from 180 to 210° C. or high-boiling mixtures of aromatic and aliphatic hydrocarbons with a boiling range of from 180 to 220° C. and/or spindle oil and/or monochloronaphthalene are used, preferably (monochloronaphthalene).

The organic oily or oil-type solvents of low volatility and with an evaporation number of above 35 and a flash point of above 30° C., preferably above 45° C., can be replaced in part by organochemical solvents of high or medium volatility, with the proviso that the solvent mixture also has an evaporation number of above 35 and a flash point of above 30° C., preferably above 45° C., and that the insecticide/fungicide mixture is soluble or emulsifiable in this solvent mixture.

In a preferred embodiment, some of the organochemical solvent or solvent mixture or an aliphatic polar organochemical solvent or solvent mixture replaced. Aliphatic organochemical solvents comprising hydroxyl and/or ester and/or ether groups are preferably used, such as, for example, glycol ethers, esters and the like.

Organochemical binders used for the purposes of the present invention are the binding drying oils and/or synthetic resins which are known per se and which can be diluted in water and/or dissolved or dispersed or emulsified in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on natural and/or synthetic resin.

The synthetic resin used as binder can be employed in the form of an emulsion, dispersion or solution. Bitumen or bituminous substances may also be used as binder, in amounts of up to 10% by weight. In addition, colorants, pigments, water repellants, odor-masking agents and inhibitors or anticorrosive agents and the like, all of which are known per se, can additionally be employed.

The composition or concentrate preferably comprises, in accordance with the invention, at least one alkyd resin or modified alkyd resin and/or a drying vegetable oil as organochemical binder. Substances which are preferably used in accordance with the invention are alkyd resins with an oil content of over 45% by weight, preferably 50 to 68% by weight.

All or some of the above mentioned binder can be replaced by a fixative (mixture) or a plasticizer (mixture). These additives are intended to prevent volatilization of the active compounds, and also crystallization or precipitation. They preferably replace 0.01 to 30% of the binder (based on 100% of the binder employed).

The plasticizers are from the chemical classes of the phthalic esters, such as dibutyl phthalate, dioctyl phthalate or benzyl butyl phthalate, phosphoric esters such as tributyl phosphate, adipic esters such as di-(2-ethylhexyl) adipate, stearates such as butyl stearate or amyl stearate, oleates such as butyl oleate, glycerol ethers or higher molecular weight glycol ethers, glycerol esters and p-toluenesulfonic esters.

Fixatives are based chemically on polyvinyl alkyl ethers such as, for example, polyvinyl methyl ether or ketones such as benzophenone and ethylenebenzophenone.

Another suitable solvent or diluent is, in particular, water, if appropriate in a mixture with one or more of the above mentioned organochemical solvents or diluents, emulsifiers and dispersants.

Particularly effective protection of wood is achieved by industrial-scale impregnating processes, for example vacuum, double-vacuum or pressure processes.

If appropriate, the ready-to-use compositions may comprise further insecticides and, if appropriate, also one or more fungicides.

Additional components are preferably the insecticides and fungicides mentioned in WO 94/29 268. The compounds mentioned in this document are expressly part of the present invention.

Most preferred components which may be mentioned are insecticides such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxide and triflumuron, and fungicides such as epoxyconazole, hexaconazole, azaconazole, propiconazole, tebuconazole, cyproconazole, metconazole, imazalil, dichlorfluanid, tolylfluanid, 3-iode-2-propynyl butylcarbamate, N-octylisothiazolin-3-one and 4,5-dichloro-N-octylisothiazolin-3-one.

The compounds according to the invention can also be employed for protecting objects which come into contact with salt water or brackish water, such as hulls, screens, nets, buildings, moorings and signaling systems, from fouling.

Fouling by sessile *Oligochaeta*, such as *Serpulidae*, and by shells and species from the *Ledamorpha* group (goose barnacles), such as various *Lepas* and *Scalpellum*species, or by species from the *Balanomorpha* group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile *Entomostraka* groups, which come under the generic term *Cirripedia* (cirriped crustaceans), is of particular importance.

Surprisingly, it has now been found that the compounds according to the invention, alone or in combination with the other active compounds, have an outstanding antifouling action.

Using the compounds according to the invention alone or in combination with other active compounds, the use of heavy metals such as, for example, in bis(trialkyltin) sulfides, tri-n-butyltin laurate, tri-n-butyltin chloride, copper (I) oxide, triethyltin chloride, tri-n-butyl(2-phenyl-4-chlorophenoxy)tin, tributyltin oxide, molybdenum disulfide, antimony oxide, polymeric butyl titanate, phenyl (bispyridine)bismuth chloride, tri-n-butyltin fluoride, manganese ethylenebisthiocarbamate, zinc dimethyldithiocarbamate, zinc ethylenebisthiocarbamate, zinc salts and copper salts of 2-pyridine-thiol 1-oxide, bisdimethyldithiocarbamoylzinc ethylenebisthiocarbamate, zinc oxide, copper(I) ethylenebisdithiocarbamate, copper thiocyanate, copper naphthenate and tributyltin halides, can be dispensed with, or the concentration of these compounds substantially reduced.

If appropriate, the ready-to-use antifouling paints can additionally comprise other active compounds, preferably algicides, fungicides, herbicides, molluscicides, or other antifouling active compounds.

Preferentially suitable co-components for the antifouling compositions according to the invention are:
  algicides such as 2-tert-butylamino-4-cyclopropylamino-6-methylthio-1,3,5-triazine, dichlorophen, diuron, endothal, fentine acetate, isoproturon, methabenzthiazuron, oxyfluorfen, quinoclamine and terbutryn;
  fungicides such as benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;

molluscicides such as fentin acetate, metaldehyde, methiocarb, niclosamid, thiodicarb and trimethacarb; or conventional antifouling active compounds such as 4,5-dichloro-2-octyl-4-isothiazolin-3-one, diiodomethylparatryl sulfone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulfonyl)pyridine, 2,4,5,6-tetrachloroisophthalonitrile, tetramethylthiuram disulfide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730–732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hard resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials in such as colophonium to allow controlled release of the active compounds. Furthermore, the paints may comprise plasticizers, modifiers which affect the rheological properties and other conventional constituents. The compounds according to the invention or the above mentioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests, either alone or in combination with other active compounds and/or auxiliaries. They are active against sensitive and resistant species and against all developmental stages. These pests include:

From the order of the *Scorpionidea*, for example *Buthus occitanus*.

From the order of the *Acarina*, for example *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the *Araneae*, for example *Aviculariidae, Araneidae*.

From the order of the *Opiliones*, for example *Pseudoscorpiones chelifer, Pseudoscorpiones cheiridium, Opiliones phalangium*.

From the order of the *Isopoda*, for example *Oniscus asellus, Porcellio scaber*.

From the order of the *Diplopoda*, for example *Blaniulus guttulatus, Polydesmus* spp.

From the order of the *Chilopoda*, for example *Geophilus* spp.

From the order of the *Zygentoma*, for example *Ctenolepisma* spp., *Lepisma saccharina, Lepismodes inquilinus*.

From the order of the *Blattaria*, for example *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the *Saltatoria*, for example *Acheta domesticus*.

From the order of the *Dermaptera*, for example *Forficula auricularia*.

From the order of the *Isoptera*, for example *Kalotermes* spp., *Reticulitermes* spp.

From the order of the *Psocoptera*, for example *Lepinatus* spp., *Liposcelis* spp.

From the order of the *Coleptera*, for example *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the *Diptera*, for example *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the *Lepidoptera*, for example *Achroia grisella, Galleria mellonella, Plodia interpunctella, Tinea cloacella, Tinea pellionella, Tineola bisselliella*.

From the order of the *Siphonaptera*, for example *Ctenocephalides canis, Ctenocephalides felis, Pulex irritans, Tunga penetrans, Xenopsylla cheopis*.

From the order of the *Hymenoptera*, for example *Camponotus herculeanus, Lasius fuliginosus, Lasius niger, Lasius umbratus, Monomorium pharaonis, Paravespula* spp., *Tetramorium caespitum*.

From the order of the *Anoplura*, for example *Pediculus humanus capitis, Pediculus humanus corporis, Phthirus pubis*.

From the order of the *Heteroptera*, for example *Cimex hemipterus, Cimex lectularius, Rhodinus prolixus, Triatoma infestans*.

In the field of the insecticides for domestic use, they are used alone or in combination with other suitable active compounds, such as phosphoric esters, carbamates, pyrethroids, growth regulators or active compounds from other known classes of insecticides.

They are used as aerosols, unpressurized spray products, for example pump and atomizer sprays, automatic fogging systems, foggers, foams, gels, evaporator products with evaporator plates made of cellulose or polymer, liquid evaporators, gel and membrane evaporators, propeller-driven evaporators, unenergized, or passive, evaporation systems, moth papers, moth bags and moth gels, as granules or dusts, in baits or in bait stations.

Representatives of the formula (I) were effective as chitinase inhibitors and/or had an insecticidal action in the biotest.

TABLE 1

Structural examples (I)

![Structure of formula I: flavin derivative with R1, R2 on benzene ring, R3 on N, R4 on N, with carbonyl groups]

| Ex. | R1 | R2 | R3 | R4 |
|---|---|---|---|---|
| 1 | $CH_3$ | $CH_3$ | $CH_2CH(OH)CH(OH)$—$CH(OH)CH_2OH$ | H |
| 2 | $CH_3$ | $CH_3$ | $CH_2CH(OH)CH(OH)$—$CH(OH)CH_2OH$ | $CH_3$ |
| 3 | $CH_3$ | $CH_2COOH$ | $CH_2CH(OH)CH(OH)$—$CH(OH)CH_2OH$ | H |
| 4 | $CH_3$ | $CH_3$ | $CH_2CH(OH)CH(OH)$—$CH(OH)CH_2OPO_3$ | H |
| 5 | $CH_3$ | $CH_3$ | $CH_2CHO$ | H |
| 6 | $CH_3$ | $N(CH_3)2$ | $CH_2CH_2CH(OH)$—$CH(OH)CH_2OH$ | H |
| 7 | $CH_3$ | —$NHCH_2CH(OH)$—$CH(OH)CH(OH)CH_2OH$ | $CH_2CH(OH)CH(OH)$—$CH(OH)CH_2OH$ | H |
| 8 | H | Cl | $C_6H_6$ | H |
| 9 | H | $NO_2$ | H | H |
| 10 | H | Cl | —$CH_2CH_2OH$ | H |
| 11 | $CF_3$ | Cl | $CH_2CH(OH)CH(OH)$—$CH(OH)CH(OH)CH_3$ | H |

Biological Example 1

Chitinase test with soluble extracts from *Lucilia cuprina* puppae

Test animals: Cytosol of *Lucilia cuprina*

The substances, which are dissolved in DMSO, are provided on 384-well microtiter plates in a concentration of 2 mM, the first four columns being empty. The substances are diluted 1:40 with 100 mM NPP pH 7.0 (50 μM). 5 μl of each of these dilutions are transferred to a 384-well test plate, starting with column 5. Into the first two columns there are pipetted in each case as negative control, into the third and fourth column in each case 5 μl of 5×10-6 M allosamidin in 2.5% DMSO in 100 mM NPP pH 7.0 5 μl 2.5% DMSO in 100 mM NPP pH 7.0 as positive control.

The substances are incubated for 20 minutes at room temperature with 2.5 μg of cytosolic extract of late *Lucilia cuprina puppae* in 10 μl of 100 mM sodium phosphate buffer pH 7.0 and 10 μl of 100 μM methylumbelliferyl (MUF-triacetylchitotriose). The reaction is quenched by addition of 25 μl of 0.5 M glycine buffer 2 M sodium hydroxide, pH 10.4. The inhibition is determined by measuring the relative fluorescence at an excitation of 360±40 nm and an emission of 460±40 nm. The test substances are evaluated in comparison with the inhibition of the enzyme by allosamidin. The inhibition of the release of MUF is a measure for the efficacy of the inhibitor. In subsequent tests, concentration series in the range of from 100 nM to 200 μM are tested, and the release of MUF is measured every 2 minutes before the reaction is quenched.

Compounds which lead to more than 50% inhibition of chitinase at maximum reaction velocity at 100 μM are assessed as effective.

For example, the following compounds showed more than 50% inhibition of the *Lucilia cuprina* endochitinase at 100 μM:

| | Ex.: 1, 6, 7 | | |
|---|---|---|---|
| Ex. | 200 μM | 100 μM | 10 μM |
| 1 | >>>50 | >>50 | >>50 |
| 6 | >>>50 | >>50 | >50 |
| 7 | >>>50 | >>50 | 50 |

Biological Example 2

Injection test with *Periplaneta* larvae

Test animals: *Periplaneta americana*, third instar

The compounds are prepared in aqueous solution (0.1 N acetic acid) and diluted as required. Using a 10 μl Hamilton syringe, 1 μl of the 20 or 2 μg were injected behind the 3rd pair of legs closely underneath the abdominal cavity of the cockroach larvae. Solvent (0.1 N acetic acid) was applied as control and 10 μg allosamidine as positive control. Batches of twenty cockroach larvae were treated per concentration and compound. On day 1, the control mortality and the initial mortality caused essentially by artificial effects during the injection were determined. If this initial mortality was less than 50%, the experiment was continued. The cockroach larvae were placed on filter paper in standard Petri dishes (9.5 cm Ø), and a quarter of a wafer was added. The ecdysis rate of the control animals and of the treated cockroach larvae was observed over a period of 23 days, and larval mortality and inhibition of ecdysis were recorded after days 1, 5 and 23. The efficacy is calculated using the following formula.

$$\frac{100 \times (\% \text{ test mortality} - \% \text{ control mortality})}{100 - \% \text{ control mortality}}$$

Preparations which showed an efficacy of more than 50% at the test concentration were considered as effective.

More than 50% mortality against *Periplaneta americana* third instars was observed in, for example, compound 1 at 2 μg.

We claim:

1. A method for controlling infesting an animal consisting essentially of the step of topically administering to said pests or topically or systemically to said animal an effective amount of flavin derivatives of the formula (I)

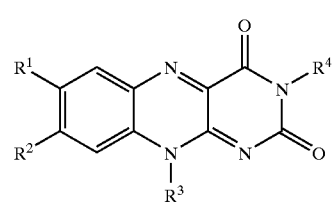

(I)

in which
R$^1$ is hydrogen, trifluoromethyl, alkyl or alkoxy,
R$^2$ is hydrogen, halogen, nitro, alkyl, alkoxy, dialkylamino, —$CH_2COOH$ or the radical $NHCH_2CH(OH)CH(OH)CH(OH)CH_2OH$,
R$^3$ is hydrogen, $CH_2CH_2CH(OH)CH(OH)CH_2OH$, $CH_2CH(OH)CH(OH)CH(OH)CH_2OH$, phenyl, —CH$_2$CHO, —CH$_2$CH$_2$OH, CH$_2$CH(OH)CH(OH)CH(OH)CH(OH)CH$_3$ or CH$_2$CH(OH)CH(OH)CH(OH)CH$_2$OPO$_3$, R$^4$ is hydrogen or alkyl and stereoisomers and salts thereof.

2. The method of claim 1, wherein

R$^1$ is methyl

R$^2$ is methyl, dimethylamino, or NHCH$_2$CH(OH)CH(OH)CH(OH)CH$_2$OH

R$^3$ is CH$_2$CH$_2$CH(OH)CH(OH)CH$_2$OH or CH$_2$CH(OH)CH(OH)CH(OH)CH$_2$OH and R$^4$ is hydrogen.

3. The method of claim 1, wherein said dialkylamino is dimethylamino.

4. A method for controlling pests consisting essentially of administering to pests and/or their environment an effective amount of flavin derivatives of the formula (I)

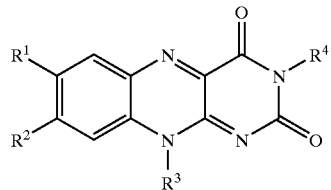

in which
R$^1$ is hydrogen, trifluoromethyl, alkyl or alkoxy,
R$^2$ is chlorine,
R$^3$ is hydrogen, CH$_2$CH$_2$CH(OH)CH(OH)CH$_2$OH, CH$_2$CH(OH)CH(OH)CH(OH)CH$_2$OH, phenyl, —CH$_2$CHO, —CH$_2$CH$_2$OH, CH$_2$CH(OH)CH(OH)CH(OH)CH(OH)CH$_3$ or CH$_2$CH(OH)CH(OH)CH(OH)CH$_2$OPO$_3$,
R$^4$ is hydrogen or alkyl
and stereoisomers and salts thereof.

* * * * *

UNITED STATES PATENT AND TRADEMARK OFFICE
CERTIFICATE OF CORRECTION

PATENT NO.    : 6,875,766 B2
DATED         : April 5, 2005
INVENTOR(S)   : Andreas Turberg et al.

It is certified that error appears in the above-identified patent and that said Letters Patent is hereby corrected as shown below:

Column 20,
Line 46, after "controlling" insert -- pests --.

Signed and Sealed this

Fourteenth Day of March, 2006

JON W. DUDAS
*Director of the United States Patent and Trademark Office*